US006460420B1

(12) United States Patent
Paul et al.

(10) Patent No.: US 6,460,420 B1
(45) Date of Patent: Oct. 8, 2002

(54) FLOWMETER FOR PRESSURE-DRIVEN CHROMATOGRAPHY SYSTEMS

(75) Inventors: Phillip H. Paul; Don W. Arnold, both of Livermore, CA (US)

(73) Assignee: Sandia National Laboratories, Livermore, CA (US)

( * ) Notice: Subject to any disclaimer, the term of this patent is extended or adjusted under 35 U.S.C. 154(b) by 0 days.

(21) Appl. No.: 09/548,474

(22) Filed: Apr. 13, 2000

(51) Int. Cl.$^7$ ............................ G01F 1/37; G01N 30/00; B01D 15/08

(52) U.S. Cl. ................. 73/861.52; 73/61.52; 210/198.2

(58) Field of Search .............. 73/61.52, 861.42–861.64; 210/198.2

(56) References Cited

U.S. PATENT DOCUMENTS

| | | | | |
|---|---|---|---|---|
| 3,250,469 A | * | 5/1966 | Colston ................. | 235/200 PF |
| 3,792,609 A | * | 2/1974 | Blair et al. ............... | 73/861.52 |
| 3,838,598 A | * | 10/1974 | Tompkins ................ | 73/861.52 |
| 4,096,746 A | * | 6/1978 | Wilson et al. ........... | 73/861.52 |
| 4,260,705 A | * | 4/1981 | Tsibris ..................... | 525/328.4 |
| 4,917,575 A | * | 4/1990 | Miller, Jr. et al. ............ | 417/52 |
| 4,961,344 A | * | 10/1990 | Rodder ......................... | 73/202 |
| 5,198,066 A | * | 3/1993 | Mimori et al. ................ | 55/523 |
| 5,314,630 A | * | 5/1994 | Kim et al. ................... | 210/794 |
| 5,431,821 A | * | 7/1995 | Olesik et al. ............... | 210/633 |
| RE35,010 E | * | 8/1995 | Price ............................. | 222/1 |
| 5,653,884 A | * | 8/1997 | Smart et al. ................. | 210/634 |
| 5,795,469 A | * | 8/1998 | Quinn et al. ............. | 210/198.2 |
| 5,832,409 A | * | 11/1998 | Ramakrishnan et al. ...... | 702/12 |

FOREIGN PATENT DOCUMENTS

JP 59-170745 * 9/1984 .......... G01N/15/08

OTHER PUBLICATIONS

Solute Transfer Through Columns of Glass Beads, DeSmedt et al, Water Resources Research v 20 n Feb. 2, 1984, P225–232.*

Coalescence of Oil–in–Water Suspensions by Flow through Porous Media, Spielman et al, Ind. Eng. Chem.., Fundam., v 16, No. 2, 1977.*

Firs–Principles Calculations of Dynamic Permeability in Porous Media, Zhou et al, Phys Rev B, v 39, No. 16, pp 12027–12039, Jun. 1, 1989.*

Model for Estimating the Hydraulic Conductivity of Granular Material, Sperry et al, Ground Water V33, N6, P892–898, Nov. 1995.*

Modelling of Porous Media by Renormalization of the Stokes Equations, Kim et al, Journal of Fluid Mechanics v 154, p 269–86.*

* cited by examiner

Primary Examiner—Hezron Williams
Assistant Examiner—J L P
(74) Attorney, Agent, or Firm—Donald A. Nissen

(57) ABSTRACT

A flowmeter for accurately measuring the flowrate of fluids in high pressure chromatography systems. The flowmeter is a porous bed of a material, the porous bed having a porosity in the range of about 0.1 to 0.6 and a pore size in the range of about 50 nm to 1 $\mu$m, disposed between a high pressure pumping means and a chromatography column. The flowmeter is provided with pressure measuring means at both the inlet and outlet of the porous bed for measuring the pressure drop through the porous bed. This flowmeter system provides not only the ability to measure accurately flowrates in the range of $\mu$L/min to nL/min but also to provide a signal that can be used for a servo loop or feedback control system for high pressure pumping systems.

7 Claims, 2 Drawing Sheets

FLOWMETER FOR PRESSURE-DRIVEN CHROMATOGRAPHY SYSTEMS

STATEMENT OF GOVERNMENT INTEREST

This invention was made with Government support under contract no. DE-AC04-94AL85000 awarded by the U.S. Department of Energy to Sandia Corporation. The Government has certain rights in the invention.

CROSS-REFERENCE TO RELATED APPLICATIONS

Not applicable.

BACKGROUND OF THE INVENTION

This invention relates generally to method and apparatus for the precise measurement of the flowrate of pressure-driven liquids and more particularly, for precisely measuring fluid flow rate, thereby providing for accurate control of the flowrate and composition, of liquids injected into high pressure liquid chromatography systems.

In liquid chromatography, chemical separations may be performed by flowing a fluid (the mobile phase) past an immobilized material (the stationary phase) inside a liquid chromatography (LC) column. By injecting a sample consisting of multiple components into one end of the LC column, allowing them to be separated into distinct bands as the sample flows through the LC column, and detecting those bands near the exit end of the LC column this technique is used for chemical analysis of mixtures. In those systems, the separation is governed by the dynamic partitioning of the analyte between the mobile phase and the stationary phase. Control of the separation may be achieved by adjusting the flowrate as well as the composition of the mobile phase or the stationary phase or both to influence analyte partitioning.

High-performance liquid chromatography (HPLC) is an established analytical technique that relies on high-pressure means, that can be mechanical pumps (generally a gear- or cam-driven pump capable of generating pressures in excess of 5,000 psi), to drive a fluid sample through a specially prepared column. The HPLC separation material or stationary phase is typically a thick bed packed with fine particles. HPLC columns can also be packed with special polymers or resins. Regardless of the column packing used, the HPLC column presents a very large resistance to flow, hence the need for high pressures to drive the sample being analyzed through the system.

Conventional HPLC systems typically employ separation columns of about 3–5 mm in diameter and flow rates ≈3–5 mL/min. However, miniaturization of the separation column (microbore columns) offers several advantages, including improved efficiency, mass detection sensitivity, low solvent consumption, small sample quantity, and easier coupling to a detector such as mass spectrometers and flame-based detectors and several analytical methods using miniaturized or capillary columns have been developed for micro-HPLC. These columns generally have inside diameters of 1 mm or less.

Gradient elution is a process that has been developed for HPLC and micro-HPLC wherein the mobile phase composition is varied during separation for separating a wide variety of complex samples. The gradient elution approach is useful when the components of the mixture have a range of properties and no single mobile phase composition is appropriate for separating all of them. In HPLC, the creation of the solvent gradient is typically accomplished by using two or more means for generating high-pressure to deliver two different fluids into a small mixing chamber. The mixed liquid is then forced into the HPLC column. The composition of the mobile phase is controlled and varied by adjusting the relative flowrate from the individual pumps to achieve gradient elution.

Low volume flowrates of varying composition are required in capillarybased separation techniques when a single mobile phase is insufficient to separate all of the chemical components of a sample. Conventional approaches of providing a variable composition mobile phase at low flowrates are expensive to implement, slow to respond to external control, and are generally unreliable in composition for flow rates of less than 1 $\mu$L/min. Although the miniaturization of separation columns offers the above-mentioned advantages, accurately and consistently delivering a $\mu$L/min gradient flow into a capillary column (e.g., 10–100 $\mu$m i. d.) packed with micrometer-size particles poses a difficult problem.

Low volume flowrates (typically in the range of nL/min to tens of nL/min) are also required for liquid chromatography/mass spectrometry (LC/MS) systems, where the output of a liquid chromatography column is injected into the input of a mass spectrometer.

Further, there is, as yet, no convenient means for handling fluctuations in the output of the high pressure pumps conventionally used in HPLC. These fluctuations can affect the flowrate of the mobile phase which, in turn, can have a deleterious effect on the analysis. Conventional means of correcting for such operational fluctuations, such as a servo loop cannot be used because the heavy damping required makes the system time response too slow to use servo control.

What is required is a system that will provide pressure driven flows at precisely measured and thus accurately controlled flowrates, wherein the flowrate can be in the range of mL/min to nL/min. Further, the system must be compatible with microbore columns and the desire for small sample quantity, low solvent consumption, improved efficiency, the ability to run samples in parallel, and field portability. In addition, it is desirable that the flowrate measuring system provide a signal that can be used for a servo loop or feedback control system for a high pressure pumping system.

SUMMARY OF THE INVENTION

It is an object of this invention to provide an apparatus for accurate measurement of the flowrate of liquids in high pressure systems.

It is a further object is to provide an apparatus for accurate measurement of the flowrate of liquids in high pressure liquid chromatography (HPLC) systems.

It is yet another object of this invention to provide for accurate measurement of liquid flowrates in micro-HPLC systems at flowrates in the range of mL/min to nL/min.

A further object is to provide for accurate control of fluid flowrate and composition of the mobile phase in gradient elution chromatography systems.

Yet another object of the invention is to provide a system of feedback control to eliminate fluctuations that can occur during the operation of high pressure generating means.

Another object is to provide a substrate having a microchannel system disposed thereon comprising at least one electrokinetic pump and associated flowmeter in combination with a chromatography column.

Another object of the invention is to provide a method for accurately measuring and controlling the flowrate of liquids in a high pressure system.

These and other objects of the present invention will become apparent from the following description and accompanying drawings.

The invention involves measuring the pressure drop through a porous bed of material disposed at the outlet of a high pressure pumping means and by the use of Darcy's Law, determining the flowrate of the pumped liquid. The pressure drop through the porous bed of material not only provides an accurate determination of the fluid flowrate but also provides for controlling the fluid flowrate. Further, the pressure drop through the porous bed of material can provide an error signal that can be used as input to a servo loop to control the pressure supplied by the high pressure pumping means and thereby eliminate fluctuations in fluid flowrate. The system provides superior performance, including faster response and higher reliability at very low flowrates ($\approx$ nL/min), and the ability to produce arbitrary gradient profiles, and can be used for a variety of applications.

BRIEF DESCRIPTION OF THE DRAWINGS

The accompanying drawings, which are incorporated into and form a part of the disclosure of the invention, illustrate embodiments of the apparatus of the invention and together with the written description serve to explain the principles of the invention. In the drawings like elements are referred to by like numbers.

DETAILED DESCRIPTION OF THE INVENTION

The present invention is directed to apparatus and method for accurately measuring and controlling the flowrate of liquids in high pressure systems. In particular, the apparatus can be used to determine flowrates in high pressure liquid chromatography (HPLC) systems where pressures can be very high (up to 40,000 psi) and flow rates can be typically low ($\mu$L/min) and thus difficult to measure accurately and control under the best of circumstances. Moreover, the apparatus is such that it can be used to provide control of fluid flow at very low flowrates ($\approx$ nL/min) such as would be required for liquid chromatography/mass spectrometry (LC/MS) systems and in capillary-based chromatography.

It is well known in the art that the flowrate of a liquid through a porous bed is given by Darcy's Law $$Q = D_p K A / \mu L$$

where:

Q is the flowrate of the liquid;

DP is the pressure difference through the porous bed, i.e., the difference between the outlet pressure and the inlet pressure;

K is the Darcy permeability of the porous bed;

$\mu$ is the dynamic viscosity of the fluid; and

A/L is the ratio of the geometric cross-sectional area to the geometric length of the porous bed.

Therefore, by measuring the pressure drop across a porous bed disposed between a high pressure pumping system and a chromatography column, it is now possible to determine accurately the flow rate of a fluid flowing into a chromatography column. Thus, the porous bed becomes a device for accurately measuring the flowrate of a fluid being delivered by a high pressure pumping system into a chromatography column. The flowrate measuring device for high pressure systems disclosed herein will hereinafter be referred to as a Darcy Flowmeter. For operation in conjunction with a chromatography column it is desirable that the material that comprises the porous bed be selected such that no chromatographic separation occurs. Thus, the material can comprise uncoated and nonporous materials known to those skilled in the art for forming porous packed beds such as glass, ceramic or polymer beads or porous monolithic polymeric material. Since the structure of the porous bed is such as to provide for electroosmotic flow but resist pressure-driven flow, it is preferred that the porosity of the porous bed be in the range of about 0.1 to 0.6 with pore sizes in the range of about 50 nm to 1 $\mu$m. Porosity is defined as the ratio of the total volume of pores in the bed to the bulk volume occupied by the bed.

Figure 1:
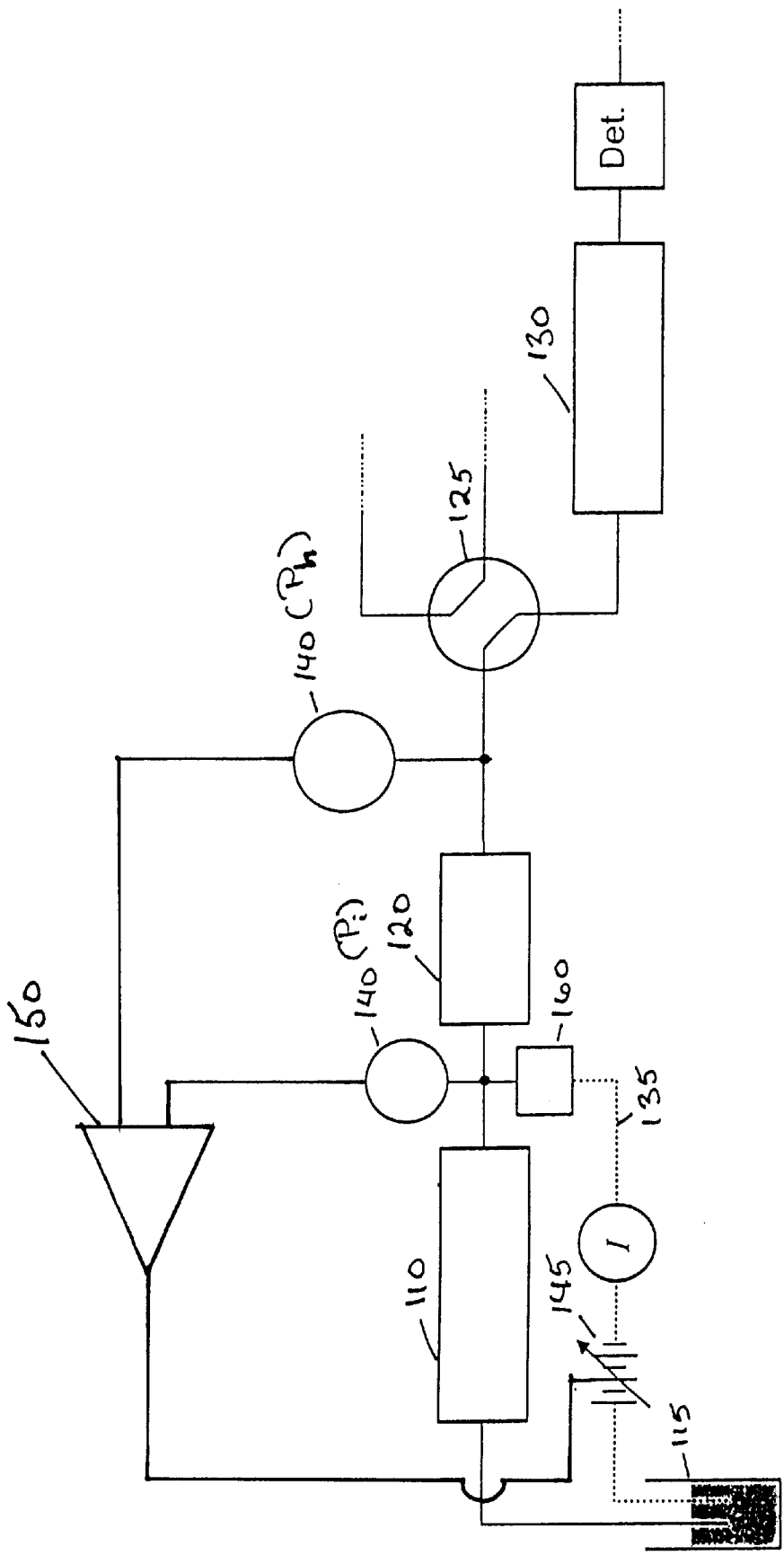
FIG. 1 is a schematic illustration of an embodiment of the present invention.

Referring now to FIG. 1, which illustrates schematically a chromatography system incorporating a Darcy Flowmeter for accurately measuring the flowrate of a buffer solution into a HPLC column. The outlet of a high pressure pumping means 110 is joined to the inlet of Darcy Flowmeter 120 and the outlet of the Darcy Flowmeter is connected to the inlet of an HPLC column 130. Means for injecting an analysis sample, such as a conventional high pressure sampling valve 125, can be incorporated between the outlet of the Darcy Flowmeter and the HPLC column 130. Pressure measuring means 140 are connected to both the inlet and outlet of Darcy Flowmeter 120 to measure the pressure drop through the porous bed. The flowrate of a buffer solution 115 forced through the HPLC column by high pressure pumping means 110 can be determined from Darcy's Law, as given above. Fluctuations in the flowrate of the buffer solution can now be detected and corrected for immediately by appropriate adjustments to the high pressure pumping means. These adjustments can be made, by way of example, by incorporating a servo or feedback loop 150 between Darcy Flowmeter 120 and high pressure pumping means 110.

In a preferred embodiment of the present invention (illustrated in FIG. 1), high pressure pumping means 110 is an electrokinetic pump (EKP). An EKP, comprises a tube or channel, that can be a capillary channel or microchannel, forming a fluid passageway containing an electrolyte and having a porous dielectric material disposed therein between one or more spaced electrodes 135. The porous dielectric material can include small particles, high surface area structures fabricated within the microchannel, or microporous materials. An electric potential that can be varied is applied between the electrodes. The source of the electric potential can be a variable power supply 145. The electrodes are in contact with the electrolyte that can be an aqueous or an organic liquid or mixtures thereof. The electric field applied across the EKP by the electrodes will cause electroosmotic flow of the electrolyte contained in the porous dielectric material and presented with an external flow resistance will create a pressure at the down stream end of the EKP. The flowrate of the electrolyte is proportional to the magnitude of the applied electric field (V/m applied across the EKP) and the pressure generated is proportional to the voltage across the device. The direction of flow of the electrolyte is determined by both the nature of the electrochemical interaction between the porous dielectric material and the electrolyte and the polarity of the applied electric potential. The EKP is a compact and efficient device that converts electric power to hydraulic power in the working fluid and has been shown to be capable of generating hydraulic pressures at least as great as 5000 psi. Because the EKP is purely a voltage-driven device there are no fluctuations in output such as those experienced by conventional high pressure pumps. Accordingly, servo loops can be used as flow control means in conjunction with EKPs. Moreover, in contrast to prior art hydraulic pumps, and HPLC pumps in particular, the present invention can be realized by integrating part or all of the described components on a chip or micro-scale device, i.e., a device wherein the components have dimensions less than about 0.1 mm. The operation of the EKP has been fully described by Paul et al. in U.S. Pat. No. 6,103,164 entitled "Electrokinetic High Pressure Hydraulic System" issued Jan. 11, 2000, incorporated herein in its entirety. In this embodiment, feedback control can be accomplished by adjusting the voltage applied to the EKP, either manually or by means of a programming device such as a computer that, in turn, adjusts the pressure applied to the downstream HPLC column.

It will be appreciated by those skilled in the art that it is desirable to eliminate the generation of any gases that could arise as a consequence of electrolysis of the EKP electrolyte. This can be accomplished by several means known to the art. By way of example, a section of ultra micro-porous material, such as the porous glass sold under the trademark VYCOR, having nominally 4 nm pores, or a membrane such as that sold under the trademark NAFION saturated with electrolyte can be interposed between the electrode providing connection to the high pressure fluid junction and the junction itself 160. The ultra micro-porous material carries the current but the pores are sufficiently fine that pressure-driven or electro-osmotic flow is negligible.

In another aspect of the present invention, the flowrate measuring device (Darcy Flowmeter) described above can be used for accurate control of fluid flow in gradient elution chromatography. Gradient elution is a process by which the mobile phase composition is varied during passage of the sample being analyzed through the chromatography column and is particularly useful for separating a wide variety of complex samples. The gradient elution approach is useful when the components of the mixture have a range of properties and no single mobile phase composition is appropriate for separating all of them.

Figure 2:
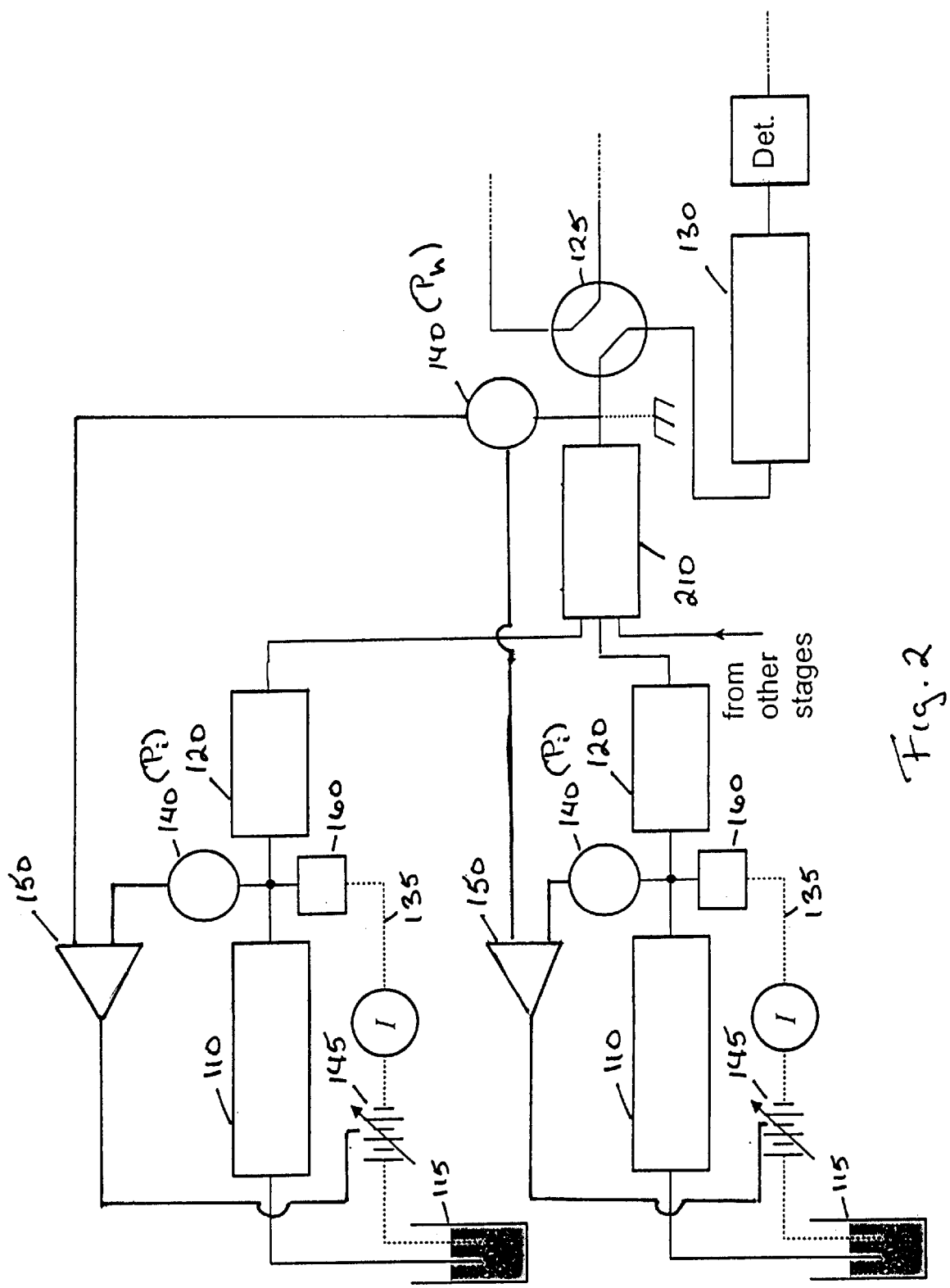
FIG. 2 shows a scheme for gradient elution chromatography employing the present invention.

In gradient elution HPLC, the creation of the solvent gradient is typically accomplished by using two or more high-pressure mechanical pumps to deliver two or more different fluids into a small mixing chamber. The composition of the mobile phase is typically controlled and varied by adjusting the relative output flows from the individual pumps to achieve a variation in composition with time. Output flows can be estimated from pump characteristics and assuming uniform output flow during the course of the chromatographic analysis. However, these estimates can often be in error due to changing pump characteristics, such that the output flow is no longer uniform, and undetected fluctuations in flow rate. In accordance with the present invention, an improved scheme for gradient elution chromatography is shown in FIG. 2

Each buffer solution 115 that together comprises the mobile phase is provided with a high pressure pumping means 110 (typically a pump capable of generating the requisite high pressure, such as an EKP) the outlet of each pumping means is joined to a Darcy Flowmeter 120, described above. The outlets of the Darcy Flowmeters are joined together at the inlet of a mixing means 210 for mixing the solutions together before injection into HPLC column 130. Mixing of the various solutions can be passive such as by simply combining the solutions in a chamber and allowing diffusion to take place. Mixing can also be by assisted mixing wherein the combined solutions are flowed through a length of porous material having a relatively open and cross-connected internal structure such as by flowing the solutions through a capillary of length of about 1 to 2 cm and packed with about 5 $\mu$m non-porous and uncoated silica beads. Active mixing can also be used to mix the combined solutions. An example of active mixing useful for rapidly and efficiently mixing liquids particularly in capillary-based analytical systems can be found in co-pending application U.S. patent application Ser. No. 09/164,863 entitled "Electrokinetic Micro-Fluid Mixer" filed Oct. 1, 1998, assigned to the same assignee, incorporated herein in its entirety. Here, mixing is accomplished by applying an electric field to each liquid, thereby inducing electroosmotic flow in each, the liquids being in contact with one another. By appropriate choice of the value of the electric field each liquid can be induced to create a zone of recirculation thereby stirring the liquid and creating interfacial area to promote molecular mixing. The electroosmotically induced fluid flow causes repeated laminar folding of the liquids to homogeneously mix the liquids together. Other types of liquid mixing systems known to those skilled in the art can also be used. Sample injection means 125 is disposed between the outlet of sample mixing means 210 and the inlet of HPLC column 130. The inlet of the HPLC column is also equipped with a downstream pressure measuring means 140 that provides both the reference pressure for the Darcy Flowmeters as well as a measure of the condition of the HPLC column. The downstream pressure measuring means can be positioned anywhere downstream of the Darcy Flowmeters providing no source of a pressure drop comparable to that in the Darcy Flowmeters is between the downstream pressure measuring means and the inlet of the HPLC column.

The flowrate through the $i^{th}$ part of the gradient elution system, i.e., that part of the system that includes a high pressure pumping means (pump) and associated Darcy Flowmeter, is given by the expression $$Q_i = (P_i - P_h) H_i$$

where $Q_i$ is the flowrate through the $i^{th}$ part of the system;

$P_i - P_h$ is the measured pressure drop through the $i^{th}$ Darcy Flowmeter, where $P_h$ is the measured pressure at the outlet of the Darcy Flowmeter (at inlet of the HPLC column) and $P_i$ is the measured pressure at the inlet of the Darcy Flowmeter (at the outlet of the $i^{th}$ high pressure pump); and $H_i$ is $K_i A_i / \mu_i L_i$, defined above.

Operation of the gradient elution system can start with the specification of a running pressure $P_h$ and the composition of the fluid mixture as a function of time (e.g., the mixture fraction of each buffer being given by $X_i = Q_i / \Sigma Q_i$). Based on a prior calibration of the system, which includes a determination of a characteristic volume $V_i = T_i Q_i$, where $T_i$ is the time required for a change in pump operation to be detected at the inlet of the HPLC column, the relationships given above can be applied to calculate directly the required pressures $P_i$ as a function of time to provide a constant flowrate of the fluid mixture through the HPLC column. Given the computed time profiles for the pressures required from each EKP, the EKP driving voltages are actively adjusted to achieve the required pressures. This adjustment of the voltages can be done by direct drive from an error signal derived from the difference between the measured pressure provided by the Darcy Flowmeter and a programmed pressure. A further advantage to the incorporation of a Darcy Flowmeter is that fluctuations that can arise in the operation of the various EKPs can be actively controlled to achieve a very low flow noise.

It is now possible to define a process for gradient elution that will provide the appropriate fluid mixture composition to the HPLC column. Moreover, this process is amenable to control by a computer, a closed loop controller, or any other means known to those skilled in the art for providing a feedback control loop. A process for supplying the appropriate mixture for gradient elution that uses an EKP as the high pressure pumping means can be summarized as follows:

1) Specify how the composition of the mixture should vary with time and the base flow rate or HPLC pressure required to perform the separation;
2) Compute the required EKP outlet pressure/time profile for each EKP;
3) Flush the system with a base buffer solution;
4) Inject the sample to be analyzed;
5) Provide the required mixture composition profile as a function of time by adjusting the voltage applied to the various EKPs while actively adjusting the flowrates by comparing the computed EKP pressure/time profile with that of the associated Darcy Flowmeter; and
6) Detect the components of the separated mixture.

It would be obvious to one skilled in the art that the flowmeter, electrokinetic pumping means, and associated chromatography apparatus could be fabricated as microstructures on a substrate thereby defining a miniaturized chromatography system such as described by Paul et al. in U.S. Pat. Nos. 6,103,164 and 6,019,882.

In summary, by measuring the pressure drop through a porous bed of material the present invention provides apparatus (Darcy Flowmeter) for accurately measuring and controlling flowrate in high pressure systems and particularly in high pressure liquid chromatography systems. The pressure drop measured by the Darcy Flowmeter can provide an error signal that can be used as input to a servo loop to control the pressure supplied by a high pressure pumping means and thereby eliminate fluctuations in flowrate. The Darcy Flowmeter is well suited to be used in conjunction with an electrokinetic pump (EKP) as the high pressure pumping means. When operated in this fashion, the error signal produced by the Flowmeter can control the voltage supplied to the EKP and thus the pressure output by the EKP.

It will be understood that the described arrangements of apparatus and the methods pertaining thereto are merely illustrative of applications of the principles of this invention and many other embodiments and modifications can be made by those of skill in the art without departing from the spirit and scope of the invention as defined in the claims.

We claim:

1. An improved chromatography apparatus in which high pressure pumping means forces a fluid through a chromatography column, wherein the improvement comprises:

a flowmeter capable of measuring flowrates in the range of $\mu$L/min to nL/min interposed between the high pressure pumping means and the chromatography column, said flowmeter comprising a porous bed of a material, wherein the porous bed has a porosity in the range of about 0.1 to 0.6 and pore sizes in the range of about 50 nm to 1 $\mu$m, and pressure measuring means disposed at a fluid inlet and a fluid outlet of the bed of porous material for measuring the pressure drop through the bed of porous material.

2. The chromatography apparatus of claim 1, wherein the material comprising the porous bed includes glass, ceramic or polymer beads or a porous monolithic polymeric material, such that substantially no chromatographic separation occurs as a consequence of the presence of this material.

3. The chromatography apparatus of claim 1, further including a feedback loop connected between the flowmeter and the high pressure pumping means.

4. The chromatography apparatus of claim 1, wherein the high pressure pumping means is an electrokinetic pump.

5. A method for accurately measuring the flowrate of a fluid in a high pressure chromatography system, comprising:

disposing a flowmeter between the outlet of a high pressure pumping means and the inlet of a chromatography column, wherein the flowmeter comprises a porous bed of a material, the porous bed having a porosity in the range of about 0.1 to 0.6 and a pore size in the range of about 50 nm to 1 $\mu$m, and pressure measuring means disposed at a fluid inlet and a fluid outlet of the porous bed for measuring the pressure drop through the porous bed.

6. An apparatus for the precise control of liquid flow rates in the range of $\mu$L/min to nL/min, comprising:

an electrokinetic pump having a fluid inlet and a fluid outlet;

a flowmeter disposed at the fluid outlet of said electrokinetic pump, wherein the flowmeter comprises a porous bed of a material and wherein the porous bed has a porosity in the range of about 0.1 to 0.6 and pore sizes in the range of about 50 nm to 1 $\mu$m, and pressure measuring means disposed at the inlet and outlet of the bed of porous material for measuring the pressure drop through the bed of porous material.

7. The apparatus of claim 6, wherein the material comprising the porous bed includes glass, ceramic or polymer beads or a porous monolithic polymeric material, such that substantially no chromatographic separation occurs as a consequence of the presence of this material.

* * * * *